United States Patent
Matheny

(10) Patent No.: US 9,132,172 B2
(45) Date of Patent: *Sep. 15, 2015

(54) COMPOSITIONS AND METHODS FOR TREATING ORGAN DYSFUNCTION

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Rosewell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,909

(22) Filed: Mar. 24, 2014

(65) Prior Publication Data

US 2014/0205565 A1    Jul. 24, 2014

Related U.S. Application Data

(60) Continuation-in-part of application No. 13/732,731, filed on Jan. 2, 2013, now abandoned, and a division of application No. 11/182,551, filed on Jul. 15, 2005, now Pat. No. 8,568,761.

(51) Int. Cl.

| | | |
|---|---|---|
| *A61L 27/36* | (2006.01) |
| *A61L 27/54* | (2006.01) |
| *A61K 35/38* | (2015.01) |
| *A61K 35/34* | (2015.01) |
| *A61K 38/39* | (2006.01) |
| *A61K 38/18* | (2006.01) |
| *A61K 45/06* | (2006.01) |
| *A61K 48/00* | (2006.01) |
| *A61K 38/20* | (2006.01) |
| *A61K 31/22* | (2006.01) |
| *A61K 31/366* | (2006.01) |
| *A61K 31/40* | (2006.01) |
| *A61K 31/4418* | (2006.01) |
| *A61K 31/505* | (2006.01) |
| *A61K 9/00* | (2006.01) |

(52) U.S. Cl.
CPC .................. *A61K 38/39* (2013.01); *A61K 31/22* (2013.01); *A61K 31/366* (2013.01); *A61K 31/40* (2013.01); *A61K 31/4418* (2013.01); *A61K 31/505* (2013.01); *A61K 35/38* (2013.01); *A61K 38/18* (2013.01); *A61K 38/1825* (2013.01); *A61K 38/1841* (2013.01); *A61K 38/20* (2013.01); *A61K 45/06* (2013.01); *A61K 48/00* (2013.01); *A61L 27/3629* (2013.01); *A61L 27/3633* (2013.01); *A61L 27/54* (2013.01); *A61K 9/0019* (2013.01); *A61L 2300/414* (2013.01); *A61L 2300/426* (2013.01); *A61L 2400/06* (2013.01)

(58) Field of Classification Search
None
See application file for complete search history.

(56) References Cited

U.S. PATENT DOCUMENTS 5,618,544 A  *  4/1997  Brown  .......................... 424/401

* cited by examiner

*Primary Examiner* — Daniel C Gamett
(74) *Attorney, Agent, or Firm* — Francis Laws Group

(57) ABSTRACT

A method of retarding cellular senescence comprising (i) providing an extracellular matrix (ECM) composition comprising ECM from an adolescent tissue source, the ECM comprising an exogenously added cytokine, and (ii) administering ECM composition to an organ with cells exhibiting cellular senescence, wherein, the cytokine interacts with at least one molecule in the ECM composition and modulates ROS production of the cells, whereby, the cellular senescence is abated.

16 Claims, 4 Drawing Sheets

COMPOSITIONS AND METHODS FOR TREATING ORGAN DYSFUNCTION

CROSS-REFERENCES TO RELATED APPLICATIONS

This application is a continuation-in-part of U.S. application Ser. No. 13/732,731, filed on Jan. 2, 2013, which is a division of U.S. application Ser. No. 11/182,551, filed on Jul. 15, 2005, now U.S. Pat. No. 8,568,761.

FIELD OF THE INVENTION

The present invention relates to compositions and methods for treating organ dysfunction. More particularly, the present invention relates to compositions and methods for treating organ dysfunction by increasing or extending the lifespan and/or retarding the rate of degradation of cells associated therewith.

BACKGROUND OF THE INVENTION

As is well known in the art, degradation of a cell can, and in many instances will, result in degradation or impairment in the physical structure and/or function of the organ associated therewith. By way of example, it is well established that degradation and death of cells can, and in many instances will, result in cardiovascular dysfunction and disease, e.g. congestive heart failure, liver dysfunction and disease, and various cancers, e.g. basal and squamous cell carcinomas, adenocarcinoma, etc.

Referring to FIG. 1, the cell cycle consists of four distinct phases: the $G_1$ phase, S phase (synthesis) and $G_2$ phase (collectively known as the interphase), and the M phase (mitosis). Activation of each phase is dependent on the proper progression and completion of the previous phase.

As discussed in detail below, the M phase is itself composed of two tightly coupled processes: mitosis, in which the cell's chromosomes are divided between the two sister cells, and cytokinesis, in which the cell's cytoplasm divides in half to form distinct cells.

After cell division, each of the daughter cells begins the interphase of a new cycle. Although the various stages of interphase are not usually morphologically distinguishable, each phase of the cell cycle has a distinct set of specialized biochemical processes that prepare the cell for initiation of cell division.

The first phase within interphase, i.e. from the end of the previous M phase until the beginning of DNA synthesis, is called the $G_1$ phase or gap. It is also referred to as the growth phase.

During this phase, the biosynthetic activities of the cell, which had been considerably slowed down during the M phase, resume at a high rate. The duration of the $G_1$ phase is highly variable, even among different cells of the same species.

The ensuing S phase commences when DNA synthesis commences; when it is complete, all of the chromosomes have been replicated, i.e. each chromosome has two (sister) chromatids. Thus, during this phase, the amount of DNA in the cell has effectively doubled, although the ploidy of the cell remains the same.

The ensuing $G_2$ phase lasts until the cell enters the M phase (or mitosis). Significant biosynthesis similarly occurs during this phase. The biosynthesis mainly involves the production and subsequent lengthening of microtubules, which are required during the process of mitosis.

The relatively brief M (or Mitotic) phase consists of two tightly coupled processes: mitosis, in which the cell's chromosomes are divided between the two sister cells, and cytokinesis, in which the cell's cytoplasm divides in half to form distinct cells; the noted nuclear division(s) often referred to as karyokinesis. The M phase is typically broken down into several distinct phases, sequentially known as prophase, prometaphase, metaphase, anaphase, and telophase.

When a cell has temporarily or reversibly stopped dividing or regenerating it is often deemed to have entered a quiescent or senescent state referred to as the $G_0$ phase.

Non-proliferative cells generally enter the senescent $G_0$ phase or state from the $G_1$ phase and may remain senescent for long periods of time, possibly indefinitely (as is often the case for neurons). This is very common for cells that are fully differentiated.

Cellular senescence was first described by Hayflick and Moorhead (1961) when they observed that normal human fibroblasts entered a state of irreversible growth arrest after serial passage in vitro. In contrast, abnormal cells, such as cancer cells, did not enter this growth arrested state and proliferated indefinitely.

The maximum number of cell divisions that a cell can undergo, termed the Hayflick limit, varies from cell type to cell type and organism. In fibroblasts, this number is about 50 divisions, after which cell division ceases.

However, some cells become senescent after fewer replication cycles as a result of DNA damage or degradation, e.g., DNA mutations, DNA oxidation and chromosome losses, which would make a cell's progeny nonviable. If the DNA damage cannot be easily repaired, the cells either age or self-destruct (i.e. apoptosis or programmed cell death).

The process of cellular senescence can also be triggered by several additional mechanisms, including telomere shortening (i.e. a form of DNA damage or degradation).

Telomeres consist of repetitive DNA elements at the end of linear chromosomes that protect chromosome ends from degradation and recombination. Due to DNA replication mechanisms and oxidative stress, telomeres become progressively shorter with each round of replication. As increasing numbers of cell division occur, the telomeres reach a critically short length, which present as double-stranded DNA breaks, resulting in telomere-initiated senescence.

The ability to modulate oxidative stress and, thereby, telomerase activity and mitochondria function, thus provides the opportunity to extend the lifespan of a living cell and, by extension the organ, tissue or entire organism associated therewith.

It is therefore an object of the present invention to provide compositions and methods to modulate oxidative stress and, thereby, telomerase activity and mitochondria function, whereby the lifespan of a living cell and, by extension the organ, tissue or entire organism associated therewith can be extended.

SUMMARY OF THE INVENTION

The present invention is directed to ECM compositions and methods for treating organ dysfunction by increasing or extending the lifespan and/or retarding the rate of degradation of cells associated therewith.

The present invention is also directed to ECM compositions and methods that can be employed to modulate (i) telomere activity, and maintain and/or repair the length and/or structural integrity of telomeres, and/or (ii) the rate/efficiency of cellular respiration provided by mitochondria and/or the total number of mitochondria per cell (mitochondrial biogenesis), and/or mitochondrial membrane potential.

In a preferred embodiment of the invention, the ECM compositions include an ECM scaffold component ("ECM material") and at least one biologically active agent, i.e. an agent or composition that induces or modulates a physiological or biological process, or cellular activity, e.g., facilitates a cellular regenerative process.

In a preferred embodiment, the ECM material is derived from a mammalian tissue source, which can comprise, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In a preferred embodiment, the ECM material comprises acellular ECM derived from an adolescent tissue source.

In some embodiments of the invention, the biologically active agent comprises a cytokine selected from the group comprising, without limitation, interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

In some embodiments of the invention, the biologically active agent comprises a statin selected from the group comprising, without limitation, atorvastatin, cerivastatin, fluvastatin, lovastatin, mevastatin, pitavastatin, pravastatin, rosuvastatin, and simvastatin.

In some embodiments of the invention, the biologically active agent comprises chitosan.

In some embodiments of the invention, the biologically active agent comprises a cell selected from the group comprising, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stern cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some embodiments of the invention, the biologically active agent comprises a growth factor selected from the group comprising, without limitation, a platelet derived growth factor (PDGF), epidermal growth factor (EGF), transforming growth factor alpha (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-α), and placental growth factor (PLGF).

In some embodiments of the invention, the biologically active agent comprises a protein selected from the group comprising, without limitation, collagen (types I-V), proteoglycans, glycosaminoglycans (GAGs), glycoproteins, cell-surface associated proteins, and cell adhesion molecules (CAMs).

In a preferred embodiment, the biologically active agent is similarly derived or cultured from an adolescent source.

In some embodiments, the bioactive agent comprises a pharmacological agent or composition. According to the invention, suitable pharmacological agents or compositions include, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
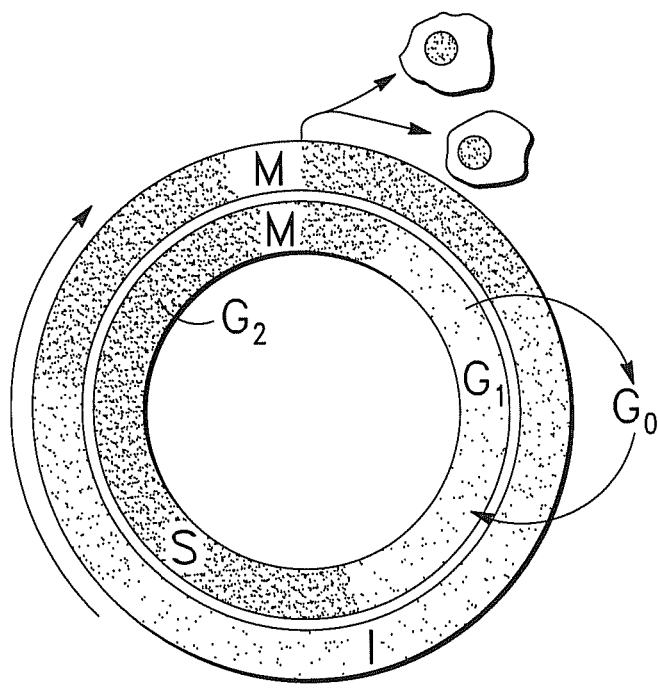
FIG. 1 is a schematic illustration of a cell cycle.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

Definitions

The term "organ dysfunction", as used herein, means and includes a reduction or impairment in physical structure or function of a mammalian organ, including, without limitation, the cardiovascular vascular system (heart and lungs), digestive system (salivary glands, esophagus, stomach, liver, gallbladder, pancreas, intestines, colon, rectum and anus), endocrine system (hypothalamus, pituitary gland, pineal body, thyroid, parathyroids and adrenals), excretory system (kidneys, ureters, bladder and urethra), immune system (lymphatic system, tonsils, adenoids, thymus and spleen), integumentary system (skin, hair and nails), muscular system, nervous system (brain and spinal cord), reproductive system (ovaries, fallopian tubes, uterus, vagina, mammary glands, prostate and penis), respiratory system (pharynx, larynx, trachea, bronchi and diaphragm) and the skeletal system (bones, cartilage, ligaments and tendons).

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dennis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The terms "biologically active agent" and "biologically active composition" are used interchangeably herein, and mean and include agent that induces or modulates a physiological or biological process, or cellular activity in vivo, in vitro, e.g., cells in a petri dish or grown in a cell culture.

The terms "biologically active agent" and "biologically active composition" thus mean and include, without limitation, the following cytokines: interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

The terms "biologically active agent" and "biologically active composition" further mean and include, without limitation, the following growth factors: platelet derived growth factor (PDGF), epidermal growth factor (EGF), transforming growth factor alpha (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-α), and placental growth factor (PLGF).

The terms "biologically active agent" and "biologically active composition" also mean and include, without limitation, the following cells: human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The term "cytokine", as used herein, means and includes a protein that acts as an intercellular mediator, such as in the generation of an immune response. The term "cytokine" thus means and includes immunomodulatory proteins, such as interlukins; particularly, interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33), and interferons, and the aforementioned peptides and polypeptides.

The term "cytokine" also means and includes the aforementioned growth factors and proteins, which act as hormonal regulators at nano- to pico-molar concentrations that facilitate cell signaling.

The terms "adolescent ECM" and "adolescent biologically active agent", as used herein, means and includes ECM and biologically active agents derived or cultured from a mammalian source that is less than 3 years of age, more preferably, a mammalian source that is less than 2 years of age, even more preferably, a mammalian source that is less than 1 year of age.

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, hormones, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, and nucleoproteins.

In some aspects of the invention, the terms "pharmacological agent", "active agent", "drug" and "active agent formulation" also mean and include one of the aforementioned "biologically active agents."

The term "anti-inflammatory", as used herein, means a "biologically active agent", "pharmacological agent" and/or "active agent formulation", which, when a therapeutically effective amount is delivered to biological tissue modulates at least one inflammatory process.

The term "anti-inflammatory" thus means and includes, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "anti-inflammatory" further means and includes selective cytokines, including, without limitation, interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

The term "pharmacological composition", as used herein, means and includes a composition comprising a "pharmacological agent" and/or a "biologically active agent" and/or any additional agent or component identified herein.

The term "ECM composition", as used herein, means and includes a composition comprising at least one ECM material.

The term "therapeutically effective", as used herein, means that the amount of the "pharmacological composition" and/or "pharmacological agent" and/or "biologically active agent" and/or ECM composition administered to biological tissue is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The teinis "delivery" and "administration" are used interchangeably herein, and mean and include providing a "pharmacological composition" or "pharmacological agent" or "biologically active agent" or "ECM composition" to a treatment site through any method appropriate to deliver the functional agent or formulation or composition to the treatment site. Non-limiting examples of delivery methods include direct injection, percutaneous delivery and topical application at the treatment site.

The terms "optional" and "optionally" mean that the subsequently described event, circumstance, or material may or may not occur or be present, and that the description includes instances where the event, circumstance, or material occurs or is present and instances where it does not occur or is not present.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to extracellular matrix (ECM) compositions and methods for treating organ dysfunction. In a preferred embodiment, the organ dysfunction is treated by increasing or extending the lifespan and/or retarding the rate of degradation of cells associated therewith.

The phrase "increasing or extending the lifespan" of a cell, as used herein, means and includes inhibiting at least senescence, apoptosis, autophagy, necrosis, mitotic catastrophe and anoikis, discussed in detail below.

As is well known in the art, there are six primary forms of cell death that can, and in many instances will, result in organ dysfunction: senescence, apoptosis, autophagy, necrosis, mitotic catastrophe and anoikis. Senescence is the halting of proliferation and entry into the Go phase where a cell remains indefinitely.

Apoptosis is programmed cell death (or suicide) that is controlled by cell signaling due to age or mild environmental stress, e.g. cells with detected DNA damage beyond repair.

Autophagy is immunogenic targeting of cells for phagocytosis characterized by a mass release of ATP and inflammatory cytokines leading to phagocytosis of a targeted cell, e.g. cells containing foreign antigens.

Necrosis is uncontrolled degradation of a cell unrecognized by the immune system, usually in response to catastrophic damage or severe lack of blood flow, e.g. ulceration.

Mitotic catastrophe is a delayed mitotic linked death due to severely damaged DNA, e.g. DNA damage due to chemical or high-energy stress.

Anoikis is also a programmed cell death process that is initiated when an anchorage cell detaches from the surrounding extracellular matrix, i.e. a detached stromal cell.

As is also well known in the art, oxidative stress is a major contributing factor associated with cellular senescence, apoptosis, autophagy, necrosis, mitotic catastrophe and anoikis, and, hence, organ dysfunction.

Figure 5:
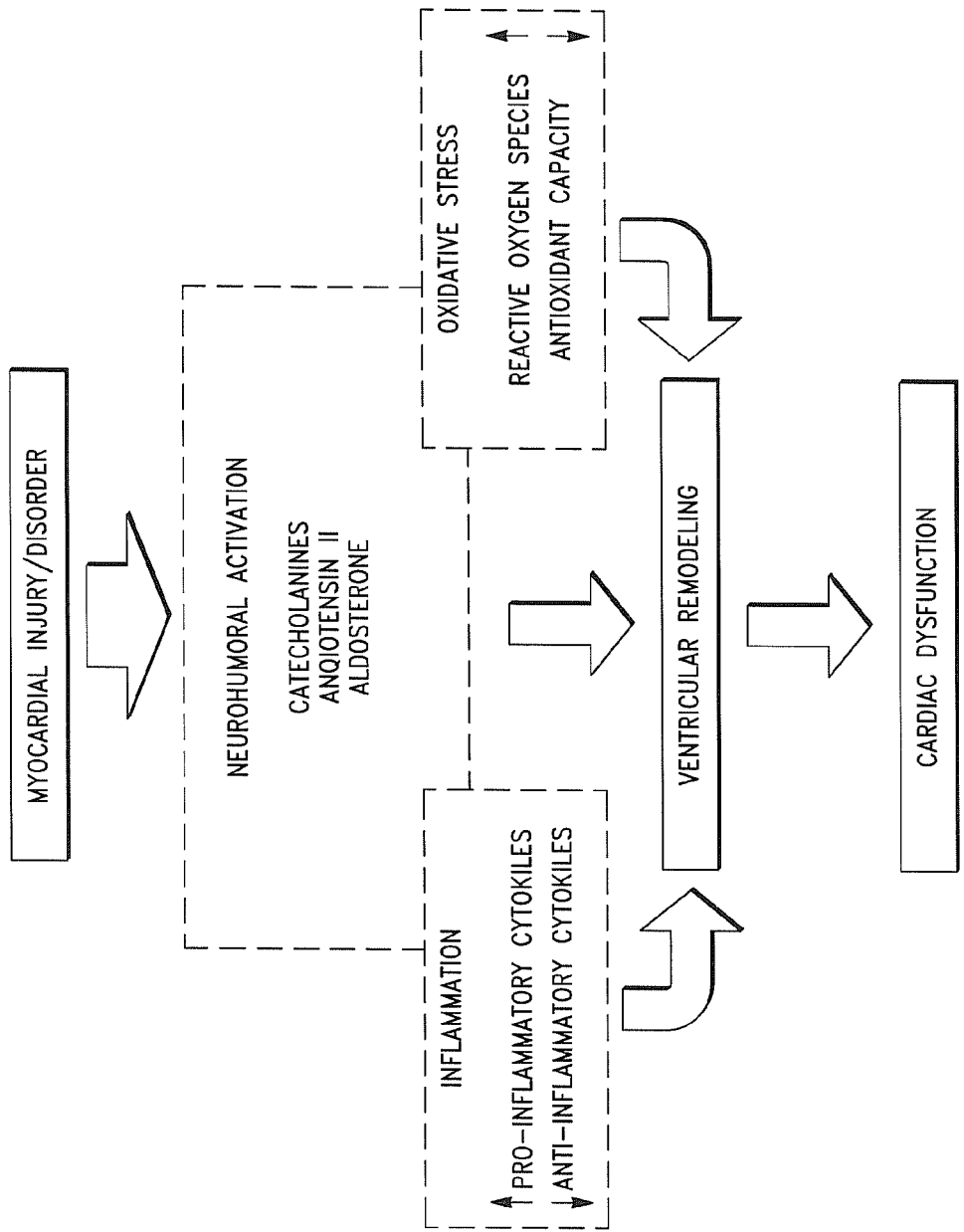
FIG. 5 is a schematic illustration of the relationship by and between oxidative stress and inflammation, and cardiac dysfunction, according to the invention.

Referring now to FIG. 5, there is shown a schematic illustration of the relationship by and between oxidative stress, inflammation and an organ dysfunction, i.e. a myocardial disorder. It is, however, to be understood that, although the organ dysfunction illustrated in FIG. 5 and discussed below is directed to a cardiac disorder, the illustrated relationship is not limited to a cardiac disorder. Indeed, according to the invention, the relationship (and treatment thereof by an ECM composition of the invention) is also applicable to other organs (and systems) and dysfunctions relating thereto, e.g. colon, urinary bladder, etc.

As illustrated in FIG. 5, activation of neurohumoral mediators, such as catecholamines, pro-inflammatory cytokines and oxidative stress all contribute to ventricular remodeling. Indeed, the increase in oxidative stress (i.e. ROS) and pro-inflammatory cytokines can not only adversely contribute to the initial myocardial injury, but also stimulate a myriad of secondary pathways that induce and/or exacerbate ventricular remodeling processes. The latter, at the organ level, includes fibrosis, and cellular apoptosis, autophagy, necrosis, mitotic catastrophe and anoikis, and, hence, organ dysfunction; in this instance, cardiac dysfunction.

Enhancing the ability of cells and organisms to resist or repair damage due to oxidative stress can thus extend the lifespan of the cells (i.e. lengthening the telomeres and/or abating degradation or shortening thereof) and healthy function of the cells and, thereby, organs associated therewith.

As indicated above, cellular senescence can be triggered by several mechanisms, including DNA damage or degradation and telomere shortening.

Telomeres consist of telomerase, a "ribonucleoprotein complex" composed of a protein component and an RNA primer sequence, which protects chromosome ends from degradation and recombination.

Due to DNA replication mechanisms and oxidative stress, telomeres become progressively shorter with each round of replication. As increasing numbers of cell division occur, the telomeres reach a critically short length, resulting in telomere-initiated senescence.

The ability to modulate oxidative stress and, thereby, telomerase activity and mitochondria function thus provides the opportunity to extend the lifespan of a living cell and, by extension the organ, tissue or entire organism.

Adenosine-5'-triphosphate (ATP) is a multifunctional nucleoside triphosphate used as a coenzyme in cells. ATP is one of the end products of photophosphorylation and cellular respiration, and is used by structural proteins in many cellular processes, including biosynthetic reactions, motility, and cell division.

Mammalian mitochondria are organelles that produce more than 90% of cellular ATP. In addition to supplying ATP, i.e. cellular energy, mitochondria are also involved in other cellular mechanisms, including cellular differentiation, apoptosis, as well as cell cycle modulation and cell growth.

Mitochondria provide intracellular ATP via a process called glycolysis, which breaks down monosaccharides into ATP through a series of biochemical processes. Mitochondria contain, among other things, the TCA cycle (also known as the Kreb cycle) enzymes that are involved in here-biosynthesis and the electron transport chain, i.e. the Oxidative Phosphorylation pathway (OxPHOS) system. Due to the large flux of redox reactions necessary to maintain oxidative phosphorylation, mitochondria are the primary site of production of reactive oxygen species (ROS).

It has, however, been found that increased production of ROS and interference with the OxPhos system can cause cell cycle arrest.

The OxPHOS system is composed of five large multi-protein enzyme complexes, which collectively transform the reducing energy of NADH and $FADH_2$ to ATP. NADH ubiquinone oxidoreductase (Complex I) contains 45 different subunits, and succinate ubiquinone reductase (Complex II), ubiquinone-cytochrome c oxidoreductase (Complex III), cytochrome c oxidase (Complex IV) and the ATP synthase (Complex V) have 4, 11, 13 and 16 subunits, respectively.

Four of the OxPHOS enzyme complexes (Complexes I, III, IV and V) have a dual genetic origin, i.e. they are composed of both nuclear DNA-encoded proteins and mitochondrial DNA-encoded proteins.

Transient ischemia (anoxia) results in the local production of extremely high levels of ROS, which can cause long term damage to mitochondria. In the initial phase of transient ischemia, oxygen is scarce, but tissue demands for ATP remain high, resulting in continued functioning of the OxPhos system except for the terminal reduction of oxygen to water by Complex IV. Therefore, reduced electron acceptors "upstream" of Complex IV accumulate to abnormally high levels.

Upon resupply of oxygen, these excess reduced carriers react directly with oxygen to generate highly toxic partially reduced oxygen species, which are capable of protein, lipid and DNA modifying reactions. The resulting oxidative damage is deemed to occur mainly inside the mitochondrion, because such radicals are so reactive that they are short lived and cannot diffuse far before finding a target for reaction.

Accordingly, OxPHOS proteins and intDNA are deemed the cellular molecules most affected by such oxidative stress. The resulting defects in intDNA and OxPHOS proteins can, and in most instances will, result in continued increased production of ROS.

However, by modulating the OxPhos system and, thereby, ROS production, which can be achieved by the ECM compositions of the invention, oxidative stress of cells can be substantially reduced or eliminated, resulting in extended lifespans of a living cells and, by extension, organs, tissue and/or entire organisms.

In a preferred embodiment, the ECM compositions modulate ROS production by modulating the rate/efficiency of cellular respiration provided by mitochondria and/or the total number of mitochondria per cell (mitochondrial biogenesis), and/or mitochondrial membrane potential, whereby the ECM compositions also modulate telomere maintenance and/or repair the length and/or structural integrity of telomeres.

As indicated above, in a preferred embodiment of the invention, the ECM compositions include at least one ECM material. According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

In a preferred embodiment, the ECM material is derived from a mammalian tissue source, which can comprise, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In a preferred embodiment of the invention, the ECM material comprises acellular adolescent ECM, i.e. ECM derived or cultured from a mammalian tissue source that is less than 3 years of age. In some aspects of the invention, the ECM material is derived from a mammalian tissue source that is less than 2 years of age. In some aspects of the invention, the ECM material is derived from a mammalian tissue source that is less than 1 year of age.

Applicant has found that ECM compositions comprising adolescent ECM provide several beneficial biochemical and cellular actions or activities. Among the beneficial biochemical and cellular actions or activities is the enhanced modulation of ROS production and, thereby modulation of telomere maintenance. Indeed, adolescent ECM is particularly effective in maintaining and/or repairing the length of telomeres.

According to the invention, the ECM material of the invention can be decellurized via various conventional decellularization processes. In a preferred embodiment, the ECM material is sterilized via applicant's proprietary novasterilis process, as disclosed in Co-Pending U.S. application Ser. No. 13/480,205; which is expressly incorporated herein in their entirety.

As set forth in U.S. Pat. No. 8,568,761, which is incorporated herein in its entirety, ECM is a scaffold matrix comprising polymerized "structural" proteins that fit into three groups: collagens, glycoproteins, and proteoglycans (which have glycosaminoglycan repeats throughout). These molecules actually polymerize to form the scaffold or matrix of proteins that exists in dynamic interaction with cells, and closely placed functional proteins (either on the cells, or bound to a structural protein).

Thus, the extracellular matrix also includes within its matrix scaffold "functional" proteins that interact with the structural proteins and with migrating or recruited cells; particularly, stem cells in tissue regeneration. The matrix functional proteins also interact with protein expressing cells during the life and maintenance of the matrix scaffold itself as it rebuilds and maintains its components. Note that some proteins fall into both a structural protein classification and a functional protein classification, depending on the protein's configuration and placement in the whole matrix.

Figure 2:
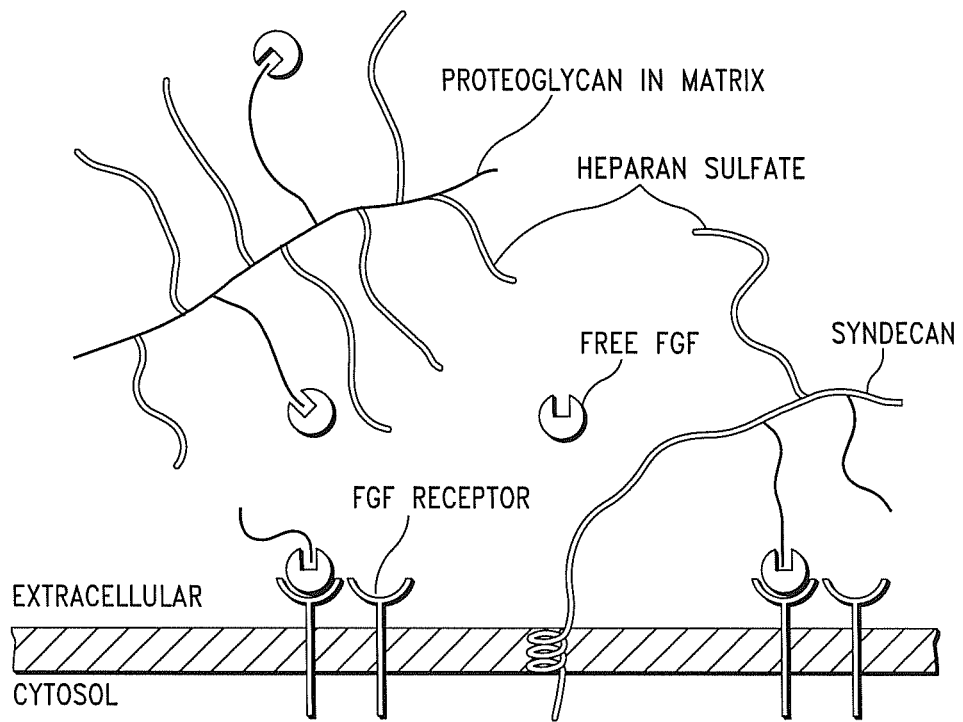
FIG. 2 is an illustration of cell-ECM interaction by and between matrix proteoglycans, glycosaminoglycans and growth factors, according to the invention.
Figure 3:
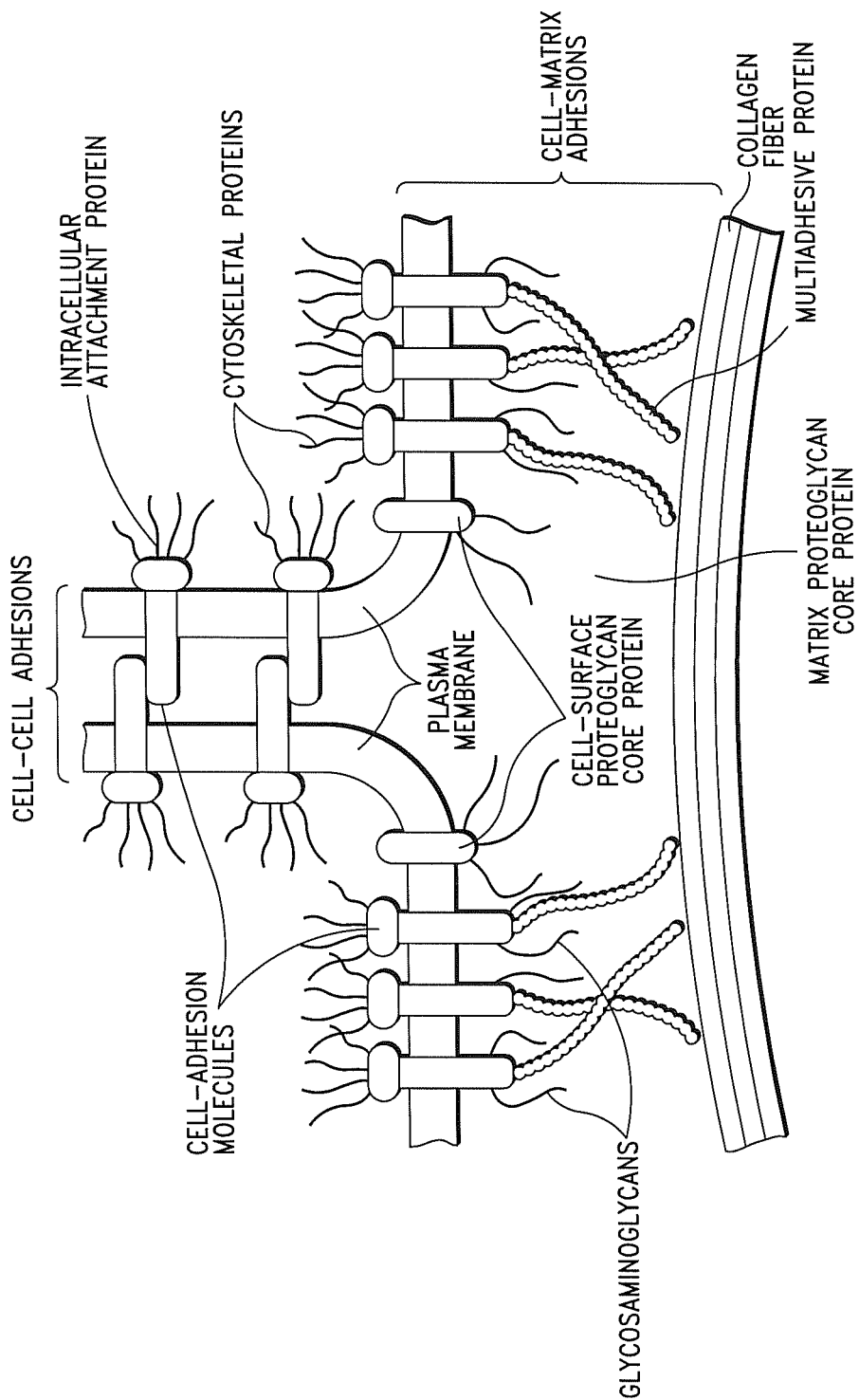
FIG. 3 is an illustration of cell-cell adhesions and cell-matrix adhesions through specific structural and functional ECM molecules, according to the invention.
Figure 4:
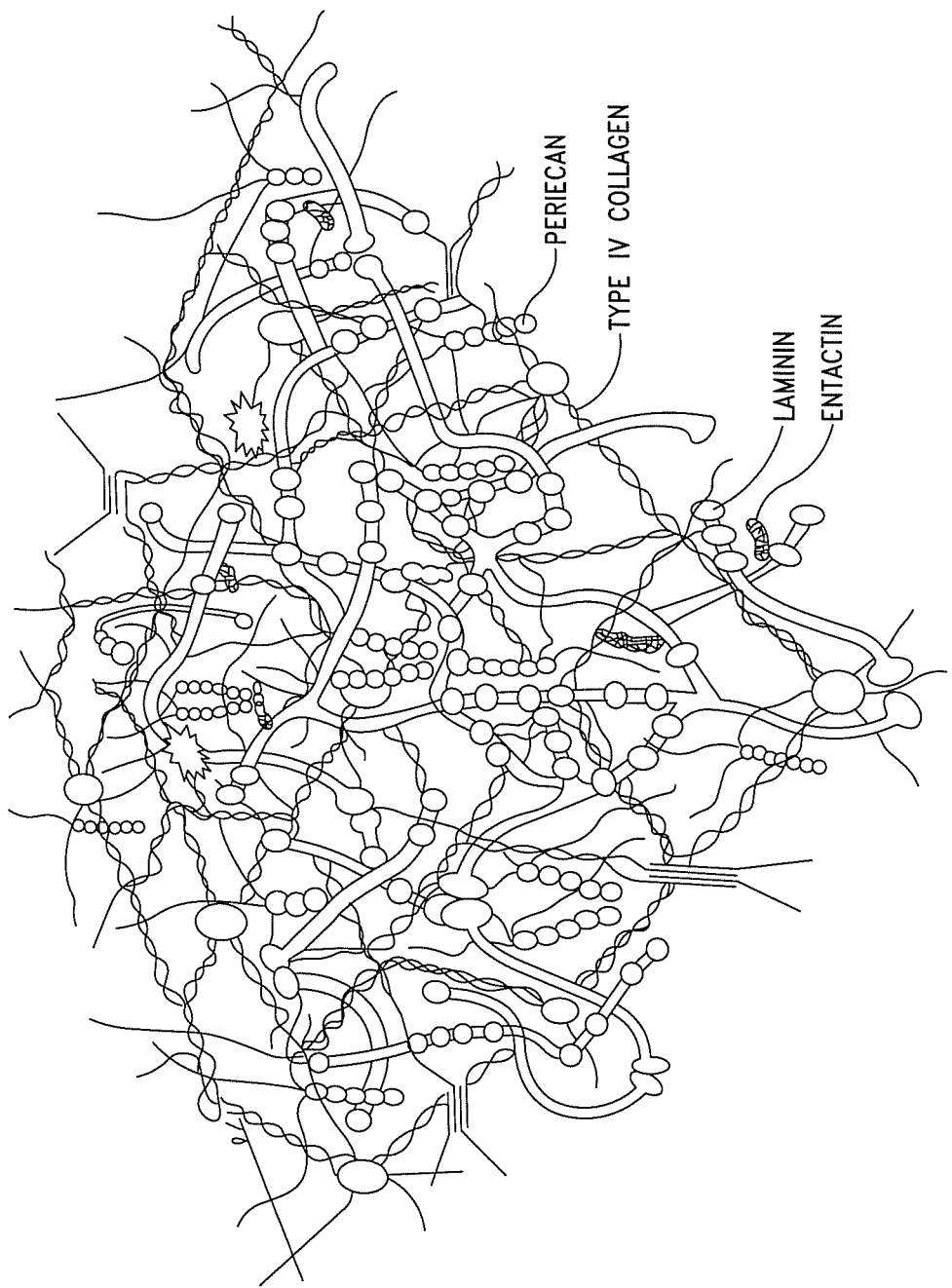
FIG. 4 is an illustration of a matrix scaffold structure, including collagen, proteoglycans and glycoproteins, according to the invention.

FIGS. 2-4 are illustrations of (i) cell-ECM interactions by and between matrix proteoglycans, glycosaminoglycans and growth factors (FIG. 2), (ii) cell-cell adhesions and cell-matrix adhesions through specific structural and functional ECM molecules (FIG. 3), and (iii) a matrix scaffold structure, including collagen, proteoglycans and glycoproteins (FIG. 4).

As also set forth in U.S. Pat. No. 8,568,761, ECM typically comprises collagen types I (which is predominant), III, IV, V, and VI, combined which are 92% of the dry weight of the matrix. Glycosaminoglycans (GAGs) include chondroitin sulfate A and B, heparan, heparin, and hyaluronic acid. Glycoproteins, such as fibronectin and entactin, proteoglycans, such as decorin and perlecan, and growth factors, such as transforming growth factor beta (TGF-$\beta$), fibroblast growth factor-2 (FGF-2) and vascular endothelial growth factor (VEGF), are key players in the activity of an ECM.

ECM typically comprises collagen types I (which is predominant), III, IV, V, and VI, combined which are 92% of the dry weight of the matrix. Glycosaminoglycans (GAGs) include chondroitin sulfate A and B, heparan, heparin, and hyaluronic acid. Glycoproteins, such as fibronectin and entactin, proteoglycans, such as decorin and perlecan, and growth factors, such as transforming growth factor beta (TGF-$\beta$), fibroblast growth factor-2 (FGF-2) and vascular endothelial growth factor (VEGF), are key players in the activity of an ECM.

The precise chemical constitution of the matrix plays a role in its function, including, for example, what collagen type is prevalent in the matrix, the pore size established by the matrix scaffold, the forces transmitted to adhesion molecules and mechanoreceptors in the cell membranes of cells at the matrix, and the forces directed from the three-dimensional environment.

During early regenerative processes, circulating cells or added cells are directed, initial temporary cell adhesion processes occur that result in embryogenesis of the cells, morphogenesis of the cells, regeneration of cell form, eventual maintenance of the cell, possible motility to another site, and organogenesis that further differentiates the cell. Facilitating these early cell adhesion functions are cell adhesion molecules (CAMs). The CAMs are available either endogenously, or, as discussed below, added as an additional component of the ECM composition.

CAMs are glycoproteins lodged in the surface of the cell membrane or transmembrane connected to cytoskeletal components of the cell. Specific CAMs include cadherins that are calcium dependent, and more than 30 types are known.

Also working as CAMs are integrins, which are proteins that link the cytoskeleton of the cell in which they are lodged to the ECM or to other cells through alpha and beta transmembrane subunits on the integrin protein. See FIG. 2 for an illustration of these interactions.

Cell migration, embryogenesis, hemostatis, and wound healing are so facilitated by the integrins in the matrix. Syndecans are proteoglycans that combine with ligands for initiating cell motility and differentiation. Immunoglobins provide any necessary immune and inflammatory responses. Selectins promote cell-cell interactions.

Collagens, the most abundant components of ECM, are homo- or heterotrimeric molecules whose subunits, the alpha chains, are distinct gene products. To date 34 different alpha chains have been identified. The sequence of the alpha chains contains a variable number of classical Gly-X-Y repetitive motifs which form the collagenous domains and noncollagenous domains. The collagenous portions of 3 homologous or heterologous alpha chains are folded together into a helix with a coiled coil conformation that constitutes the basic structure motif of collagens.

Characteristically, collagens form highly organized polymers. Two main classes of molecules are formed by collagen polymers: the fibril-forming collagens (collagens type I, II, III, V, and XI) and the non-fibrillar collagens that are a more heterogeneous class. Fibril collagen molecules usually have a single collagenous domain repeated the entire length of the molecule, and non-fibrillar collagen molecules have a mixture of collagenous and noncollagenous domains. On this basis several more subgroups of the collagen family are identified: e.g. the basement membrane collagens (IV, VIII, and X).

In addition, most all the different types of collagen have a specific distribution. For example, fibril forming collagens are expressed in the interstitial connective tissue.

The most abundant component of basement membranes is collagen IV. The multiplexins, collagens XV and XVIII are also localized to the basement membranes.

Matrix metalloproteases (MMPs) break down the collagen molecules in the ECM so that new collagen can be used to remodel and renew the ECM scaffold. It is also believed that the proteolytic activity of MMPs augment the bioavailability of growth factors sequestered within the ECM, and can activate latent secreted growth factors like TGF-beta and IGF from IGFBPs and cell surface growth factor precursors. MMPs can proteolytically cleave cell surface growth factors, cytokines, chemokine receptors and adhesion receptors, and thus participate in controlling responses to growth factors, cytokines, chemokines, as well as cell-cell and cell-ECM interactions.

Proteoglycans are grouped into several families, and all have a protein core rich in glycosoaminoglycans. Proteoglycans control proliferation, differentiation, and motility. The lecticans interact with hyaluronan and include aggrecan, versican, neurocan, and brevican. Versican stimulates proliferation of fibroblasts and chondrocytes through the presence in the molecule of EGF-like motifs.

The second type of proteoglycans have a protein core with leucine-rich repeats, which form a horse shaped protein good for protein-protein interactions. Their glycosoaminoglycan side chains mostly comprise chondroitin/dermatan sulphate or keratin sulphate. Decorin, biglycan, fibromodulin, and keratocan are members of this family. Decorin is involved in modulation and differentiation of epithelial and endothelial cells. In addition, transforming growth factor beta (TGF beta) interacts with members of this family.

There are also part-time proteoglycans, comprising CD44 (a receptor for hyaluronic acid), macrophage colony stimulating factor, amyloid precursor protein and several collagens (IX, XII, XIV, and XVIII).

The last family of proteoglycans is the heparan sulfate proteoglycans, some of which are located in the matrix, and some of which are on cell membranes. Perlecan and agrin are matrix heparan sulfate proteoglycans found in basement membranes. The syndecans and glypicans are membrane-associated heparan sulfate proteoglycans.

Syndecans have a heparan sulfate extracellular moiety that binds with high affinity cytokines and growth factors, including fibroblast growth factor (FGF), hepatocyte growth factor (HGF), platelet-derived growth factor (PDGF), heparin-binding epidermal growth factor (HB-EGF), and vascular endothelial growth factor (VEGF).

Glycoproteins are also structural proteins of ECM. The glycoprotein fibronectin (Fn) is a large dimer that attracts stem cells, fibroblasts and endothelial cells to a site of newly forming matrix. Tenascin is a glycoprotein that has Fn repeats and appears during early embryogenesis then is switched off in mature tissue.

Other glycoprotein components of ECM include elastin that forms the elastic fibers and is a major structural component along with collagen and fibrillins, which are a family of proteins consisting almost entirely of endothelial growth factor (EGF)-like domains, and laminin. Small glycoproteins present in ECM include nidogen/entactin and fibulins I and II.

The glycoprotein laminin is a large protein with three distinct polypeptide chains. Together with type IV collagen, nidogen, and perlecan, laminin is one of the main components of the basement membrane. Laminin isoforms are synthesized by a wide variety of cells in a tissue-specific manner. Laminin I contains multiple binding sites to cellular proteins.

Virtually all epithelial cells synthesize laminin, as do small, skeletal, and cardiac muscle, nerves, endothelial cells, bone marrow cells, and neuroretina. Laminins affect nearby cells, by promoting adhesion, cell migration, and cell differentiation. They exert their effects mostly through binding to integrins on cell surfaces. Laminins 5 and 10 occur predominantly in the vascular basement membrane and mediate adhesion of platelets, leukocytes, and endothelial cells.

In addition to the structural matrix proteins discussed above, specific interactions between cells and the ECM are mediated by functional proteins of the ECM, including transmembrane molecules, mainly integrins, some members of the collagen family, some proteoglycans, glycosaminoglycan chains, and some cell-surface associated proteins. These interactions lead to direct or indirect control of cellular activities within the extracellular matrix scaffold such as adhesion, migration, differentiation, proliferation, and apoptosis.

Glycosaminoglycans (GAGs) are glycosylated post-translational molecules derived from proteoglycans. GAGs include heparin, hyaluronic acid, heparan sulfate, and chondroitin sulfate A, B, and C. Heparin chains stimulate angiogenesis, and act as subunits in a proteoglycan to stimulate the angiogenic effects of fibroblast growth factor-2 (FGF-2) (also known as basic FGF or bFGF). Chondroitin sulfate B (dermatan sulfate) interacts with TGF-beta to control matrix formation and remodeling.

The extracellular portion of integrins bind fibronectin, collagen and laminin, and act primarily as adhesion molecules. Integrin-ligand binding also triggers cascades of activity for cell survival, cell proliferation, cell motility, and gene transcription.

Tenascins include cytotactin (TN-C). Cell surface receptors for tenascins include integrins, cell adhesion molecules of the Ig superfamily, a transmembrane chrondroitin sulfate proteoglycan (phosphacan) and annexin II. TN-C also interacts with extracellular proteins, such as fibronectin and the lecticans (the class of extracellular chondroitin sulphate proteoglycans including aggrecan, versican, and brevican).

Structural or functional matrix proteins that are included in the ECM materials of the invention thus include, minimally, collagens I and III, elastin, laminin, MMPs, CD44, hyaluronan, syndecan, bFGF, HGF, PDGF, VEGF, Fn, tenascin, heparin, heparan sulfate, chondroitin sulfate B, integrins, decorin, and TGF-β.

According to the invention, the ECM material of the invention can be used in whole or in part, so that, for example, an ECM material can contain just the basement membrane (or transitional epithelial layer) with the subadjacent tunica propria, the tunica submucosa, tunica muscularis, and tunica serosa. The ECM material can contain any or all of these layers, and thus could conceivably contain only the basement membrane portion, excluding the submucosa; provide, however, that the ECM material contains the active extracellular matrix portions that support cell activity and/or development.

According to the invention, the ECM compositions of the invention can also comprise ECM material from two or more mammalian tissue sources. Thus, the ECM compositions can comprise combinations of ECM material from such sources as, for example, but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart ECM material, dermal matrix, and, in general, ECM material from any mammalian fetal tissue. The ECM material sources can also comprise different mammalian animals or an entirely different species of mammals.

The ECM material can also comprise mixed solid particulates. The ECM material can also be formed into a particulate and fluidized, as described in U.S. Pat. Nos. 5,275,826, 6,579,538 and 6,933,326, to form a mixed emulsion, mixed gel or mixed paste.

According to the invention, the liquid or semi-solid components of the ECM compositions (i.e. gels, emulsions or pastes) can comprise various concentrations. Preferably, the concentration of the liquid or semi-solid components of the ECM compositions are in the range of about 0.001 mg/ml to about 200 mg/ml. Suitable concentration ranges thus include, without limitation: about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml and about 40 mg/ml. to about 42 mg/ml.

The noted concentration ranges are, however, merely exemplary and not intended to be exhaustive or limiting. It is understood that any value within any of the listed ranges is deemed a reasonable and useful value for a concentration of a liquid or semi-solid component of an ECM composition.

According to the invention, the dry particulate or reconstituted particulate that forms a gel emulsion or paste of the two ECM materials can also be mixed together in various proportions. For example, the particulates can comprise 50% of small intestine submucosa mixed with 50% of pancreatic basement membrane. The mixture can then similarly be fluidized by hydrating in a suitable buffer, such as saline.

As also indicated above, in a preferred embodiment of the invention, the ECM compositions further include at least one exogenously added biologically active agent.

In a preferred embodiment, the biologically active agent is similarly derived from an adolescent mammalian tissue source.

In a preferred embodiment, the biologically active agent facilitates or supports modulation of telomere activity and/or the maintenance and/or repair of telomere length and/or the structural integrity of telomeres.

In some embodiments of the invention, the biologically active agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo ®, Pitava®), pravastatin (Pravachol®, Selektine®, Lipostat®), rosuvastatin (Crestor®), and simvastatin (Zocor®, Lipex®). Several actives comprising a combination of a HMG-CoA reductase inhibitor and another agent, such as ezetimbe/simvastatin (Vytorin®), are also suitable.

Applicant has found that when one of the noted HMG-CoA reductase inhibitors; particularly, cerivastatin, is added to an ECM composition having one of the aforementioned ECM materials, the HMG-CoA reductase inhibitor links to and interacts with the ECM material, wherein, when the ECM composition is delivered to biological tissue the ECM compositions provides several beneficial biochemical and cellular actions or activities. Among the beneficial biochemical and cellular actions or activities is the enhanced modulation of ROS production via Rac-1 reduction.

The ECM/ HMG-CoA reductase inhibitor composition is particularly effective when the ECM comprises adolescent ECM and includes, minimally, proteoglycans, transforming growth factor-β (TGF-β) fibroblast growth factor-2 (FGF-2) and vascular endothelial growth factor (VEGF).

According to the invention, the amount of a HMG-CoA reductase inhibitor added to an ECM composition of the invention is preferably less than 20 mg, more preferably, less than approximately 10 mg.

In some embodiments of the invention, the biologically active agent comprises a cytokine selected from the group comprising, without limitation, interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

Applicant has also found that when one of the noted cytokines is added to an ECM composition having one of the aforementioned ECM materials, the cytokine links to and interacts with at least one molecule in the ECM material, particularly, TGF-β, wherein, when the ECM composition is delivered to biological tissue, the TGF-β drives an anti-inflammatory response by inhibiting macrophage maturation, whereby modulation of ROS production is similarly enhanced.

Specifically, the enhanced modulation of ROS production is achieved via inhibition of NF-κB (Nuclear Factor Kappa-Light-Chain-Enhancer of Activated B cells), which is a rapid-acting DNA transcription factor. NF-κB upregulates genes responsible for T-Cell maturation and subsequent Th1 inflammatory immune response, and, hence increased production of cytotoxic ROS.

IL-10 has particularly been shown to reduce macrophage production of reactive oxygen radicals, and thereby decreasing inflammation. See, e.g., Khaper, et al., *Targeting the Vicious Inflammation—Oxidative Stress Cycle for the Management of Heart Failure, Antioxidants and Redox Signaling*, vol. 13 (7), pp. 1033-1039 (2010). Thus, in some embodiments of the invention, the cytokine comprises IL-10.

The ECM/cytokine composition is similarly particularly effective when the ECM comprises adolescent ECM and further includes, minimally, proteoglycans, transforming growth factor-α (TGF-α), fibroblast growth factor-2 (FGF-2) and vascular endothelial growth factor (VEGF), and the cytokine comprises at least 0.1 wt. % of the ECM composition.

In some embodiments of the invention, the biologically active agent comprises chitosan. Applicant has further found that an ECM composition comprising one of the aforementioned ECM materials and chitosan is also highly effective in modulating the presence of ROS and, thereby, oxidative damage to the OxPhos system.

According to the invention, the amount of chitosan added to an ECM composition of the invention is preferably less than 50 ml, more preferably, less than approximately 20 ml.

In some embodiments of the invention, the biologically active agent comprises one of the aforementioned cells, including, without limitation, human embryonic stem cells, fetal cardiomyocytes, myofibroblasts, mesenchymal stem cells, autotransplated expanded cardiomyocytes, adipocytes, totipotent cells, and pluripotent cells.

In some embodiments of the invention, the biologically active agent comprises one of the aforementioned growth factors, including, without limitation, a transforming growth factor-alpha (TGF-α), transforming growth factor-beta (TGF-β), fibroblast growth factor-2 (FGF-2), basic fibroblast growth factor (bFGF), vascular epithelial growth factor (VEGF) and hepatocyte growth factor (HGF).

In some embodiments of the invention, the biologically active agent comprises one of the aforementioned proteins, including, without limitation, proteoglycans, glycosaminoglycans (GAGs), glycoproteins, cell-surface associated proteins, and cell adhesion molecules (CAMs).

In a preferred embodiment of the invention, the exogenously added biologically active agent comprises at least 0.05 wt. %, more preferably, at least 0.1 wt. % of the ECM composition.

According to the invention, the ECM compositions of the invention can further include one or more pharmacological agents or components to facilitate the cellular regenerative process.

In some embodiments, the bioactive agent comprises a pharmacological agent or composition. Suitable pharmacological agents or compositions, include, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

According to the invention, the amount of a pharmacological agent added to an ECM composition of the invention will, of course, vary from agent to agent. For example, in one embodiment, wherein the pharmacological agent comprises dicloflenac (Voltaren®), the amount of dicloflenac included in the ECM composition is preferably in the range of 10 μg-75 mg.

In some embodiments of the invention, the pharmacological agent specifically comprises one of the aforementioned anti-inflammatory agents.

According to the invention, the amount of an anti-inflammatory added to an ECM composition of the invention can similarly vary from anti-inflammatory to anti-inflammatory. For example, in one embodiment of the invention, wherein the pharmacological agent comprises ibuprofen (Advil®), the amount of ibuprofen included in the ECM composition is preferably in the range of 100 μg-200 mg.

According to the invention, the biologically active agents referenced above can comprise any form. In some embodiments of the invention, the biologically active agents, e.g. simvastatin and/or chitosan, comprise microcapsules that provide delayed delivery of the agent contained therein.

As will be readily appreciated by one having ordinary skill in the art, the ECM compositions can be readily employed to treat various organ dysfunctions by modulating ROS production and, thereby extending the lifespan and/or retarding the rate of degradation of cells associated with the organ.

Indeed, as discussed in detail above, the ECM compositions effectively modulate telomere activity by modulating the rate/efficiency of cellular respiration provided by mitochondria and/or the total number of mitochondria per cell (mitochondrial biogenesis), and/or mitochondrial membrane potential.

In some embodiments of the invention there is thus provided ECM compositions that include an ECM material and at least one biologically active agent, which, when administered to a mammalian organ, modulate ROS production and extend the lifespan and/or retard the rate of degradation of cells associated with the organ.

In some embodiments of the invention there is also provided a method of treating an organ dysfunction by administering an ECM composition of the invention to the organ, wherein cell function is restored, i.e. degradation of the cells associated therewith is abated and/or the lifespan of the cells is extended.

As indicated above, the dysfunction can be associated with various organs and systems, including various myocardial disorders. The organ dysfunction can also comprise a skeletal disorder, e.g. a bone marrow disorder. In this instance, the subject's bone marrow can be replaced or infused with an ECM composition of the invention; particularly, an ECM composition comprising an adolescent ECM material to effectively treat the disorder.

In some instances, treatment of the skeletal disorder can be further enhanced by augmenting the ECM composition with a chemotherapy agent. According to the invention, suitable chemotherapy agents include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibodies, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

Suitable chemotherapy agents thus include, without limitation, the following well know chemotherapy drugs: Actinomycin D, Adriamycin, Alkeran, Ara-C, Arsenic Trioxide (Trisenox), Avastin, BiCNU, Busulfan, Carboplatinum, CCNU, Cisplatinum, Cytoxan, Daunorubicin, DTIC, 5-FU, Erlotinib, Fludarabine, Gemcitabine, Herceptin, Hydrea, Idarubicin, Ifosfamide, Irinotecan, Lapatinib, Leustatin, 6-MP, Methotrexate, Mithramycin, Mitomycin, Mitoxantrone, Navelbine, Nitrogen Mustard, Rituxan, 6-TG, Taxol, Taxotere, Topotecan, Velban, Vincristine, VP-16, Xeloda.

EXAMPLES

The following examples are provided to enable those skilled in the art to more clearly understand and practice the present invention. They should not be considered as limiting the scope of the invention, but merely as being illustrated as representative thereof.

Example 1

A forty-five (45) year old male patient presents with premature liver failure. A cell sample is secured from the patient's liver and analyzed. The analysis indicates that the cells in the liver had entered a senescent phase.

An ECM composition of the invention comprising adolescent extracellular matrix comprising small intestine submucosa and an exogenously added cytokine comprising interlukin-10 (IL-10) is administered to the liver of the patient.

Sixty (60) days after the ECM composition is administered a further cell sample was secured from the patient's liver. The post-ECM composition administration analysis reflects that the rate of degradation of the liver cells has ceased. The analysis further reflects that the length of the telomeres associated with the cells has increased.

As will readily be appreciated by one having ordinary skill in the art, the present invention provides numerous advantages compared to prior art methods and systems for treating organ dysfunction. Among the advantages are the following:

The provision of extracellular matrix (ECM) compositions and methods that effectively treat organ dysfunction by increasing or extending the lifespan and/or retarding the rate of degradation of cells associated therewith.

The provision of ECM compositions that modulate the rate/efficiency of cellular respiration provided by mitochondria and/or the total number of mitochondria per cell (mitochondrial biogenesis), and/or mitochondrial membrane potential.

The provision of ECM compositions that modulate telomere activity, and maintain and/or repair the length and/or structural integrity of telomeres.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for treating organ dysfunction, comprising:
an extracellular matrix (ECM) composition comprising ECM from a mammalian tissue source comprising small intestine submucosa, said ECM comprising endogenous proteoglycans, transforming growth factors-β (TGF-β), fibroblast growth factors-2 (FGF-2) and vascular endothelial growth factor (VEGF), said ECM further comprising an exogenously added cytokine, said cytokine comprising at least 0.1% by weight of said composition,
said cytokine being linked to said ECM, wherein, when said composition is administered to biological tissue, said cytokine interacts with at least one molecule in said ECM composition, wherein said ECM composition modulates ROS production and, thereby, telomere activity.

2. The composition of claim 1, wherein said cytokine is selected from the group consisting of interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

3. The composition of claim 1, wherein said mammalian tissue source comprises an adolescent tissue source.

4. The composition of claim 1, wherein said ECM composition further comprises an exogenously added growth factor selected from the group consisting of a transforming growth factor-alpha (TGF-α), transforming growth factor-beta (TGF-β), fibroblast growth factor-2 (FGF-2), basic fibroblast growth factor (bFGF), vascular epithelial growth factor (VEGF) and hepatocyte growth factor (HGF).

5. The composition of claim 1, wherein said ECM composition further comprises an exogenously added HMG-CoA reductase inhibitor selected from the group consisting of atorvastatin, cerivastatin, fluvastatin, lovastatin, mevastatin, pitavastatin, pravastatin, rosuvastatin, and simvastatin.

6. A composition for treating mammalian organ dysfunction, comprising:

an extracellular matrix (ECM) composition comprising ECM from a mammalian tissue source comprising mesothelial tissue, said ECM comprising endogenous proteoglycans, transforming growth factors-β (TGF-β), fibroblast growth factors-2 (FGF-2) and vascular endothelial growth factor (VEGF), said ECM further comprising an exogenously added cytokine, said cytokine comprising at least 0.1% by weight of said composition, said cytokine being linked to said ECM, wherein, when said composition is administered to biological tissue, said cytokine interacts with at least one molecule in said ECM composition, wherein said ECM composition modulates ROS production and, thereby, telomere activity.

7. The composition of claim 6, wherein said cytokine is selected from the group consisting of interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

8. The composition of claim 6, wherein said mammalian tissue source comprises an adolescent tissue source.

9. The composition of claim 6, wherein said ECM composition further comprises an exogenously added growth factor selected from the group consisting of a transforming growth factor-alpha (TGF-α), transforming growth factor-beta (TGF-β), fibroblast growth factor-2 (FGF-2), basic fibroblast growth factor (bFGF), vascular epithelial growth factor (VEGF) and hepatocyte growth factor (HGF).

10. The composition of claim 6, wherein said ECM composition further comprises an exogenously added HMG-CoA reductase inhibitor selected from the group consisting of atorvastatin, cerivastatin, fluvastatin, lovastatin, mevastatin, pitavastatin, pravastatin, rosuvastatin, and simvastatin.

11. A method of retarding cellular senescence of an organ, comprising the steps of:

providing an extracellular matrix (ECM) composition, said ECM composition comprising ECM from an adolescent tissue source, said ECM comprising endogenous proteoglycans, transforming growth factors-β (TGF-β), fibroblast growth factors-2 (FGF-2) and vascular endothelial growth factor (VEGF), said ECM further comprising an exogenously added cytokine, said cytokine comprising at least 0.1% by weight of said composition; and administering said ECM composition to an organ with cells exhibiting cellular senescence, wherein, said cytokine interacts with at least one molecule in said ECM composition, wherein said ECM composition modulates ROS production of said cells and, wherein, said cellular senescence is abated.

12. The method of claim 11, wherein said tissue source comprises small intestine submucosa.

13. The method of claim 11, wherein said tissue source comprises mesothelial tissue.

14. The method of claim 11, wherein said cytokine is selected from the group consisting of interleukin-4 (IL-4), interleukin-5 (IL-5), interleukin-6 (IL-6), interleukin-9 (IL-9), interleukin-10 (IL-10), interleukin-13 (IL-13), interleukin 31 (IL-31), and interleukin-33 (IL-33).

15. The method of claim 11, wherein said ECM composition further comprises an exogenously added growth factor selected from the group consisting of a transforming growth factor-alpha (TGF-α), transforming growth factor-beta (TGF-β), fibroblast growth factor-2 (FGF-2), basic fibroblast growth factor (bFGF), vascular epithelial growth factor (VEGF) and hepatocyte growth factor (HGF).

16. The method of claim 11, wherein said ECM composition further comprises an exogenously added HMG-CoA reductase inhibitor selected from the group consisting of atorvastatin, cerivastatin, fluvastatin, lovastatin, mevastatin, pitavastatin, pravastatin, rosuvastatin, and simvastatin.

* * * * *